United States Patent
Shirai et al.

(12)

(10) Patent No.: US 6,632,975 B1
(45) Date of Patent: Oct. 14, 2003

(54) METHOD FOR THE PRODUCTION OF IN VIVO MODEL OF HEPATOCELLULAR CARCINOMA WITHOUT LUNG METASTASIS

(75) Inventors: Tomoyuki Shirai, Aichi (JP); Mitsuru Futakuchi, Aichi (JP)

(73) Assignee: Kabushiki Kaisha Daiyu-Kai Institute of Medical Science, Ichinomiya (JP)

( * ) Notice: Subject to any disclaimer, the term of this patent is extended or adjusted under 35 U.S.C. 154(b) by 0 days.

(21) Appl. No.: 09/680,931

(22) Filed: Oct. 10, 2000

(30) Foreign Application Priority Data

Jan. 20, 2000 (JP) .......................... 2000-012183

(51) Int. Cl.$^7$ .................... A01K 67/00; A01K 67/033
(52) U.S. Cl. ..................... 800/10; 424/9.1; 424/9.2; 424/9.33
(58) Field of Search .............. 800/3, 8, 9, 10; 424/9.2, 9.33, 9.1

(56) References Cited

PUBLICATIONS

Murai et al., Induction of hepatocellular carcinoma with high metastatic potential in WS/Shi rats: Discovery of an inbred strain highly susceptible to the liver carcinogen N–nitrosomorpholine, 2000, Oncology Research, vol. 12, pp. 121–126.*

Lijinsky, Metastasizing tumors in rats treated with alkylating carcinogens, 1995, Carcinogenesis, vol. 16, pp. 675–681.*

Masui et al., Highly metastatic heptocellular carcinomas induced in male F344 rats treated with N–nitrosomorpholine in combination with other hepatocarcinogens show a high incidence of p53 gene mutations . . . , 1997, Cancer Letters, vol. 112, pp. 33–45.*

Lijinsky et al., Dose response study with N–nitrosomorpholine in drinking water of F–344 rats, 1988, Cancer Research, vol. 48, pp. 2089–2095.*

Author Unknown, IARC monographs on the evaluation of the carcinogenic risk of chemicals to humans: some N–nitroso compounds, 1978, IARC, pp. 263–280.*

Futakuchi et al., "Establishment of an In Vivo Highly Metastatic Rat Hepatocellular Carcinoma Model", 1999, JP. J. Cancer Res., vol. 90, pp. 1196–1202.

Futakuchi, M., Lijinsky, W., Hasegawa, R., Hirose, M., Ito, N., Shirai, T., *Effects of Low Dose Mixtures of Four N–Nitroso Compounds on Hepatic Foci Development in the Rat*, Cancer Letters 106 (1996) 263–269.

Hasegawa, R., Futakuchi, M., Mizoguchi, Y., Yamaguchi, T., Shirai, T., Ito, N., Lijinsky, W., *Studies of Initiation and Promotion of Carcinogenesis by N–Nitroso Compounds*, Cancer Letters 123 (1998) 185–191.

* cited by examiner

*Primary Examiner*—Scott D. Priebe
*Assistant Examiner*—Brian Whiteman
(74) *Attorney, Agent, or Firm*—Oblon, Spivak, McClelland, Maier & Neustadt, P.C.

(57) ABSTRACT

The present invention provides a method for producing an in vivo model of hepatocellular carcinoma without lung metastasis in an animal by injecting diethylnitrosamine and administering nitrosomorpholine in the drinking water of the animal, as well as, methods of identifying an antimetstatic agent using the in vivo model.

19 Claims, 3 Drawing Sheets

INCIDENCES OF HEPATOCELLULAR CARCINOMA
AND LUNG METASTASIS

| INJECTED SUBSTANCES AND A METHOD OF INJECTION | INCIDENCES OF HEPATOCELLULAR CARCINOMA | INCIDENCES OF LUNG METASTASIS | SURVIVAL RATE |
|---|---|---|---|
| INTRAPERITONEAL INJECTION OF DEN | 5/5 (100%) | 0/5 (0%) | 100% |
| ADMINISTRATION OF DEN IN DRINKING WATER | 0/15 (0%) | 0/15 (0%) | 100% |
| INTRAPERITONEAL INJECTION OF NMOR | 12/13 (92%) | 1/13 (8%) | 80% |
| BOTH INTRAPERITONEAL INJECTION OF DEN AND ADMINISTRATION OF NMOR IN DRINKING WATER | 13/13 (100%) | 9/13 (69%) | 30% |

*FIG. 1*

METHOD FOR THE PRODUCTION OF IN VIVO MODEL OF HEPATOCELLULAR CARCINOMA WITHOUT LUNG METASTASIS

BACKGROUND OF THE INVENTION

1. Field of the Invention

The present invention relates to a method for the production of an in vivo lung metastatic hepatoma model, which may be useful in the search for and evaluation of antimetastatic agents.

2. Background of the Invention

Metastasis is one of the most malignant phenotypic expressions of carcinoma, and the inhibition of metastasis is the ultimate goal of anticancer therapy.

However, current antimetastatic studies using in vivo models, that is, animal models, have metastasis produced through an extremely artificial process. For example, tumor tissue itself or tumor cells have been administered by subcutaneous or intraperitoneal injection, or via direct intravenous injection to nude mice, i.e., animals whose rejection immunity is artificially removed or weakened. It is clear, however, that individual defense mechanism such as immunopotency or drug pharmacokinetics change according to the developmental stage of primary lesion or degree of systemic distribution of tumor tissue in individuals. Thus, the establishment of an animal model which represents the natural course of carcinoma in the human body, that is, an animal model where metastasis would be formed after development of carcinoma, has been highly desired.

Nevertheless, there is currently no such animal model that represents the natural course of carcinoma in the human body, that is, an animal model where lung metastasis would be formed after development of hepatoma with great efficiency. Accordingly, such an animal model would be extremely useful in the development of anticancer therapies.

SUMMARY OF THE INVENTION

It an object of the present invention to provide a model which represents the natural course of carcinoma in the human body, that is, an animal model where metastasis are formed after development of carcinoma.

The object of the present invention may be accomplished with a method of producing an in vivo model of lung metastatic hepatoma, comprising administering an effective amount of at least one nitroso compound to an animal for a time sufficient to produce lung metastatic hepatoma in the animal.

In the inventive method, administration of the hepatic carcinogen, i.e., nitroso compounds, to the animals allows induction of hepatoma in animals with great efficiency. Moreover, the present invention provides for metastasis formation in the lung after development of hepatoma. In other words, the obtained model is a metastasis model which represents the natural course of carcinoma where the whole host reactions in the host body against carcinoma are incorporated including development of hepatoma and metastasis formation. Thus, the model provided by the method of the present invention is a useful model to determine the inhibitory effect on lung metastasis of hepatoma.

Thus, the present invention can provide, with great efficiency, a model which may allow elucidation of mechanism of carcinoma metastasis in the body from more practical view points. Moreover, evaluation of the effect of the host on tumor cells and adverse effects on other organs allow development of antimetastatic agents which can be readily applicable to clinical practices.

As described above, the present invention provides a method for the production of in vivo lung metastatic hepatoma model which allows not only development of hepatoma and formation of lung metastasis with great efficiency but also evaluation of metastasis modification effect during the period of lung metastasis formation of hepatoma.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying Figures, wherein:

FIG. 1 is a table showing incidences of hepatocellular carcinoma and lung metastasis according to Example 1;

DETAILED DESCRIPTION OF THE INVENTION

Figure 2:
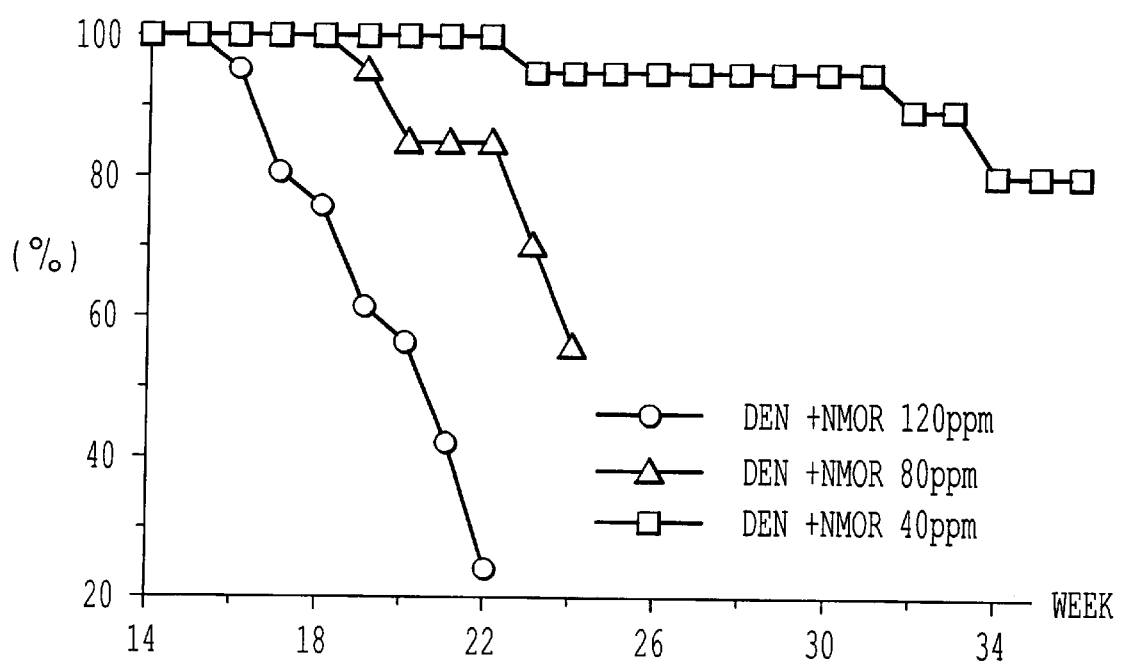
FIG. 2 is a graphical presentation of the survival rates of animals after administration of nitroso compounds according to Example 2.

As used herein the term "animal" refers to any non-human animal. The animal may be, for example, a rodent. Among rodents, rats, mice or hamsters are preferred.

It is preferable to administer the nitroso compounds to the animals by intraperitoneal injection. In another embodiment, it is preferable to administer the nitroso compounds to the animals by adding the compound to the drinking water consumed by the animal. Either procedure is easy to perform and can induce hepatocellular carcinoma and lung metastasis.

It is preferable to administer the nitroso compounds to the animals by intraperitoneal injection and by mixing the compounds in the drinking water consumed by the animals. Administration of the nitroso compounds in this manner provides induction of hepatocellular carcinoma and lung metastasis with great efficiency.

Intraperitoneal injection can be performed before, during or after administration by mixing the nitroso compounds in the drinking water. It is preferable to give injection before administration by mixing with drinking water.

The preferred dose of the above mentioned nitroso compounds by injection is 50 to 200 mg/kg body weight. This range includes all specific values and subranges therebetween, including 75, 100, 125, 150 and 175 mg/kg body weight. A dose less than 50 mg/kg body weight is likely to make it difficult to induce lung metastatic hepatocellular carcinoma. A dose over 200 mg/kg body weight may cause death of animals due to toxicity of nitroso compounds.

A preferable concentration of the above mentioned nitroso compounds in drinking water is 40 to 120 ppm. This range includes all specific values and subranges therebetween, including 50, 60, 70, 80, 90, 100 and 110 ppm. A concentration of less than 40 ppm may make it difficult to induce carcinoma, while a concentration of over 120 ppm may frequently induce hepatoma other than hepatocellular carcinoma, that is, sarcoma.

A preferable dose of the nitroso compounds by injection is 50 to 200 mg/kg body weight, with the desirable concentration of the above mentioned nitroso compounds in drinking water of 40 to 120 ppm. Such a dosing can induce lung metastatic hepatoma (hepatocellular carcinoma) with great efficiency. If either dose or concentration is less than the above mentioned preferred range, it may become difficult to induce carcinoma, while if either dose or concentration is over the above mentioned desirable range, hepatoma (hepatic sarcoma) may be induced with great efficiency.

It is preferred to give intraperitoneal injection of nitrosoamine one to five times. Injection of six or more times may induce sarcoma in the liver or cause animal death due to toxicity. Specifically, single intraperitoneal injection of nitrosoamine is highly preferred.

It is preferred to administer one to five kinds of nitrosoamine by mixing in water. Specifically, administration of single kind of nitrosoamine by mixing in water is highly preferred. Administration of two or more kinds of nitrosoamine may cause animal death due to toxicity before development of hepatoma (hepatocellular carcinoma).

Examples of nitroso compounds which may be used in this invention include nitrosodimethylamine, nitrosodiethylamine, dipropylnitrosoamine, dibutylnitrosoamine, diamylnitrosoamine, nitrosopyrolidine, nitrosopiperidine, nitrosomorpholine, nitrosomethylmorpholine, nitrosodimethylmorpholine, nitrosodiethanolamine, nitrosooxazolidine, nitrosomethyloxazolidine, nitrosodimethyloxazolidine, nitrosotetrahydrooxazolidine, and N-methyl-N'-nitro-N-nitrosoguanidine.

It is preferred to use diethylnitrosoamine as a nitroso compound to be administered by injection. It is preferred to use nitrosomorpholine as a nitroso compound to be administered by mixing with the animal's drinking water.

EXAMPLES

Having generally described this invention, a further understanding can be obtained by reference to certain specific examples which are provided herein for purposes of illustration only and are not intended to be limiting unless otherwise specified.

A method of the production of in vivo lung metastatic hepatoma model relating to the preferred embodiment of this invention is described below.

Example 1

In this example, an in vivo lung metastatic hepatoma model was produced to evaluate development of hepatoma and lung metastasis.

Animals used in this example were F344 Fisher rats (purchased from Charles River Japan Inc.).

Diethylnitrosoamine (hereinafter, referred to as "DEN") and nitrosomorpholine (hereinafter, referred to as "NMOR") were purchased from Tokyo Kasei Kogyo Co., Ltd.

DEN was diluted with physiological saline, and intraperitoneally injected in animals at a dose of 100 mg/kg body weight, or it was diluted with tap water to make the concentration of 50 ppm and administered via drinking water feeding bottle. NMOR was diluted with tap water to make the concentration of 120 ppm, and administered via a drinking water feeding bottle.

In this example, the administration method of nitroso compounds as well as development of hepatoma and lung metastasis were evaluated.

Animals were divided into four groups and treated as follows: Animals of the first group were given 50 ppm of DEN in drinking water for 16 weeks, and were sacrificed and subjected to autopsy in week 16. Animals of the second group were given 100 mg/kg body weight of DEN via intraperitoneal injection at the start of the experiment, and were sacrificed and subjected to autopsy in week 22. Animals of the third group were given 120 ppm of NMOR in drinking water for 22 weeks, and were sacrificed and subjected to autopsy in week 22. Animals of the fourth group were given 100 mg/kg body weight of DEN via intraperitoneal injection at the start of the experiment were given NMOR from the start to week 22 of the experiment, and were sacrificed and subjected to autopsy in week 22.

Liver and lung as well as other tissues were collected, fixed in formalin and stained with hematoxylin-eosin by the standard method to prepare specimens. Specimens were microscopically examined for presence of hepatocellular carcinoma in the liver and metastatic lesion in the lung to determine incidences of hepatocellular carcinoma and lung metastasis, which are shown in FIG. 1.

As shown in FIG. 1, a single intraperitoneal injection of DEN induced neither hepatoma nor metastatic lesion in the lung. Administration of DEN in drinking water induced hepatoma in 100% of animals, although no lung metastasis was observed in the animals. Administration of NMOR in drinking water induced hepatoma in 100% of animals, although lung metastasis was observed in only one animal. When animals were treated with both intraperitoneal injection of DEN and administration of NMOR in drinking water, hepatoma developed in 100%, and lung metastasis was observed in as high as 69% of animals.

In conclusion, the results presented above demonstrate that the combination of intraperitoneal injection and administration in drinking water is preferred to produce lung metastasis at a higher level.

As shown in FIG. 1, the survival rate was as low as 30% in the DEN plus NMOR treated group. Thus, the experiment described in the following Example 2 was conducted for the purpose of improving the survival and evaluating the dose dependency of the lung metastasis rate.

Example 2

Animals were given intraperitoneal injection of 100 mg/kg body weight of DEN followed by administration of 120, 80 or 40 ppm of NMOR for 14 weeks, and were sacrificed and autopsied after 14, 16, 22, 24, or 32 weeks to evaluate changes over time in hepatocellular carcinoma and lung metastatic lesion. The same methods as in Example 1 were used for sacrifice and autopsy of animals as well as preparation of specimens.

Figure 3:
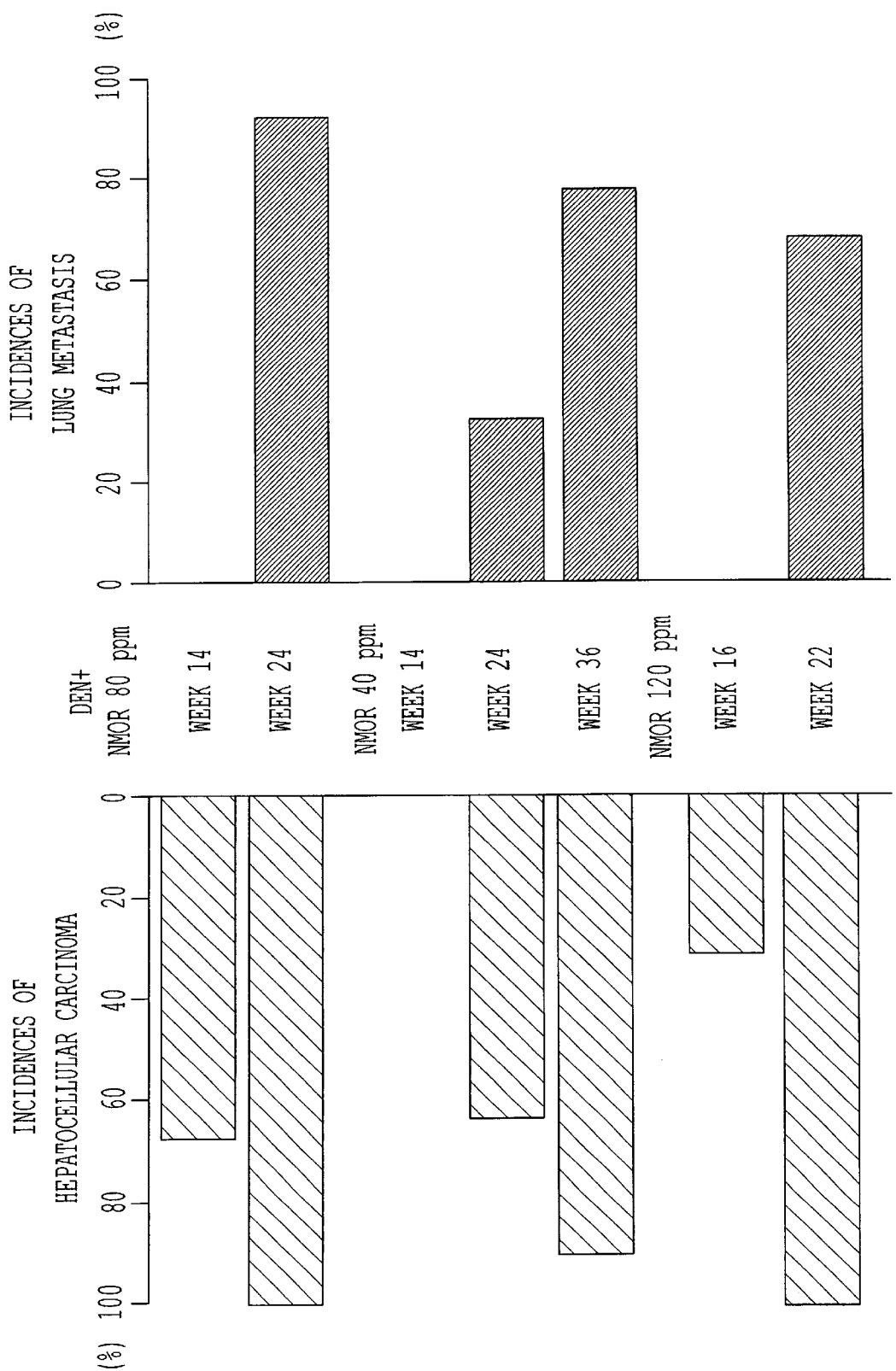
FIG. 3 is a graphical presentation of incidences of hepatocellular carcinoma and lung metastasis according to Example 2.

FIG. 2 shows survival rates of animals after administration of DEN plus NMOR. FIG. 3 shows incidences of hepatocellular carcinoma and lung metastasis.

As a result, as shown in FIG. 2, the survival rate showed a sudden decrease starting in week 14 in animals treated with 120 ppm of NMOR, and its survival rate in week 22 was 25%. On the contrary, a slight improvement in the survival rate was observed in animals treated with 80 ppm of NMOR with the rate of 58% in week 24. A greater improvement in the survival rate was observed in animals treated with 40 ppm of NMOR with the rate of 80% in week 36.

As shown in FIG. 3, hepatocellular carcinoma was detected in 67% of rats treated with DEN plus 80 ppm of NMOR in week 14, while lung metastasis was not observed at that point. In week 24, hepatocellular carcinoma and lung metastasis was observed in 100% and 92% of animals, respectively. In rats treated with DEN plus 120 ppm of NMOR, heptacellular carcinoma was detected in 31% in week 16, while lung metastasis was not observed at that point. In week 22, heptacellular carcinoma and lung metastasis was observed in 100% and 69% of animals, respectively.

In rats treated with DEN plus 40 ppm of NMOR, hepatocellular carcinoma was not detected in week 14, while it was detected in 63% and 89% of animals in week 24 and 36, respectively. Lung metastasis was observed in 33% and 78% of animals in week 24 and 36, respectively.

The incidence and lesion number of lung metastasis in rats treated with DEN plus 80 ppm of NMOR in week 24 were not largely different from those in animals treated with 40 ppm of NMOR in week 36.

These results indicate that administration of two kinds of hepatic carcinogens, DEN and NMOR, in animals can induce lung metastatic hepatoma, and that it is possible to construct a new experimental system which allows delayed period of lung metastasis formation and long term administration of antimetastatic agent.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. 12183/2000, filed on Jan. 20, 2000, and incorporated herein by reference in its entirety.

We claim:

1. A method of producing an in vivo model of hepatocellular carcinoma without lung metastasis in a rat, comprising injecting from 50 to 200 mg/kg of diethylnitrosoamine into the intraperitonium of the rat; followed by administering nitrosomorpholine to the rat by mixing 40 to 120 ppm of the nitrosomorpholine into drinking water consumed by the rat for a time sufficient to produce hepatocellular carcinoma without lung metastasis in the rat.

2. The method of claim 1, wherein 75 to 175 mg/kg of diethylnitrosoamine is injected into the intraperitonium.

3. The method of claim 1, wherein 100 to 150 mg/kg of diethylnitrosoamine is injected into the intraperitonium.

4. The method of claim 1, wherein 75 to 125 mg/kg of diethylnitrosoamine is injected into the intraperitonium.

5. The method of claim 1, wherein the injecting is performed up to five times.

6. The method of claim 1, wherein 50 to 110 ppm of nitrosomorpholine is mixed into the drinking water consumed by the rat.

7. The method of claim 1, wherein 60 to 100 ppm of nitrosomorpholine is mixed into the drinking water consumed by the rat.

8. The method of claim 1, wherein 70 to 90 ppm of nitrosomorpholine is mixed into the drinking water consumed by the rat.

9. The method of claim 1, wherein the nitrosomorpholine is administered for 14 weeks after the injection of diethylnitrosoamine.

10. A method of identifying an antimetastic agent comprising, producing an in vivo model of hepatocellular carcinoma without lung metastasis in a rat, comprising
(a) injecting from 50 to 200 mg/kg of diethylnitrosoamine into the intraperitonium of the rat;
(b) followed by administering nitrosomorpholine to the rat by mixing 40 to 120 ppm of the nitrosomorpholine into drinking water consumed by the rat for a time sufficient to produce hepatocellular carcinoma without lung metastasis in the rat;
(c) administering an agent to the rat; and
(d) detecting the onset of lung metastasis in the rat, wherein a delayed or reduced onset of lung metastasis in the rat compared to a rat model of hepatocellular carcinoma without lung metastasis produced as in step (a) and (b) in which the agent in step (c) has not been administered is indicative of an antimetastatic effect by the agent.

11. The method of claim 10, wherein 75 to 175 mg/kg of diethylnitrosoamine is injected into the intraperitonium.

12. The method of claim 10, wherein 100 to 150 mg/kg of diethylnitrosoamine is injected into the intraperitonium.

13. The method of claim 10, wherein 75 to 125 mg/kg of diethylnitrosoamine is injected into the intraperitonium.

14. The method of claim 10, wherein the injecting is performed up to five times.

15. The method of claim 10, wherein 50 to 110 ppm of nitrosomorpholine is mixed into the drinking water consumed by the rat.

16. The method of claim 10, wherein 60 to 100 ppm of nitrosomorpholine is mixed into the drinking water consumed by the rat.

17. The method of claim 10, wherein 70 to 90 ppm of nitrosomorpholine is mixed into the drinking water consumed by the rat.

18. The method of claim 10, wherein the nitrosomorpholine is administered for 14 weeks after the injection of diethylnitrosoamine.

19. The method of claim 18, wherein the agent is administered to the rat after the 14 week period following the injection of diethylnitrosoamine.

* * * * *